US006486232B1

(12) United States Patent
Wise et al.

(10) Patent No.: US 6,486,232 B1
(45) Date of Patent: *Nov. 26, 2002

(54) BIOERODIBLE POLYMERIC SEMI-INTERPENETRATING NETWORK ALLOYS FOR INTERNAL FIXATION DEVICES AND BONE CEMENTS

(75) Inventors: Donald L. Wise, Belmont; Joseph D. Gresser, Brookline; Debra J. Trantolo, Princeton; Yung-Yueh Hsu, Acton, all of MA (US)

(73) Assignee: Cambridge Scientific, Inc., Belmont, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/663,612

(22) Filed: Sep. 18, 2000

Related U.S. Application Data

(60) Continuation-in-part of application No. 09/168,129, filed on Oct. 7, 1998, now Pat. No. 6,153,664, which is a division of application No. 08/844,378, filed on Apr. 18, 1997, now Pat. No. 6,071,982.

(51) Int. Cl.$^7$ .............................................. A61L 24/08
(52) U.S. Cl. ...................... 523/118; 524/113; 524/114
(58) Field of Search ............................... 523/113, 114, 523/115, 116, 117, 118

(56) References Cited

U.S. PATENT DOCUMENTS

| 4,722,948 A | * | 2/1988 | Sanderson | 523/114 |
|---|---|---|---|---|
| 4,843,112 A | * | 6/1989 | Gerhart et al. | 523/114 |
| 4,888,413 A | * | 12/1989 | Domb | 523/113 |
| 5,286,763 A | * | 2/1994 | Gerhart et al. | 523/113 |
| 5,733,951 A | * | 3/1998 | Yaszemski et al. | 523/114 |
| 5,837,752 A | * | 11/1998 | Shastri et al. | 523/116 |
| 5,847,046 A | * | 12/1998 | Jiang et al. | 523/116 |
| 6,071,982 A | * | 6/2000 | Wise et al. | 523/114 |
| 6,124,373 A | * | 9/2000 | Peter et al. | 523/113 |

* cited by examiner

*Primary Examiner*—Peter Szekely
(74) *Attorney, Agent, or Firm*—Weingarten, Schurgin, Gagnebin & Lebovici LLP

(57) ABSTRACT

A bioerodible polymeric material, and in particular a semi-interpenetrating network ("semi-IPN") alloy, is disclosed. A beneficial end use of this material is in the form of internal fixation devices (IFDs) (such as bone supports, plates, and pins) and as cured bone cements for bone repair. A multi-part bioerodible cement system, which, upon mixing of the system parts, forms a cured bioerodible cement, includes, in one part, a first bioerodible polymer (e.g., PLGA) capable of producing acidic products upon hydrolytic degradation, and, in another part, a second bioerodible scaffolding polymer (e.g., PPF) which upon crosslinking provides a biopolymeric scaffolding or internal reinforcement for the cured cement. In another aspect, a bone cement system of the invention includes a bioerodible scaffolding polymer (such as PPF), which when polymerized provides a hardened bone cement, the cement system further including a gas generating agent in stabilized form for providing the cured bone cement with pores for facilitating inward cell migration.

41 Claims, 6 Drawing Sheets

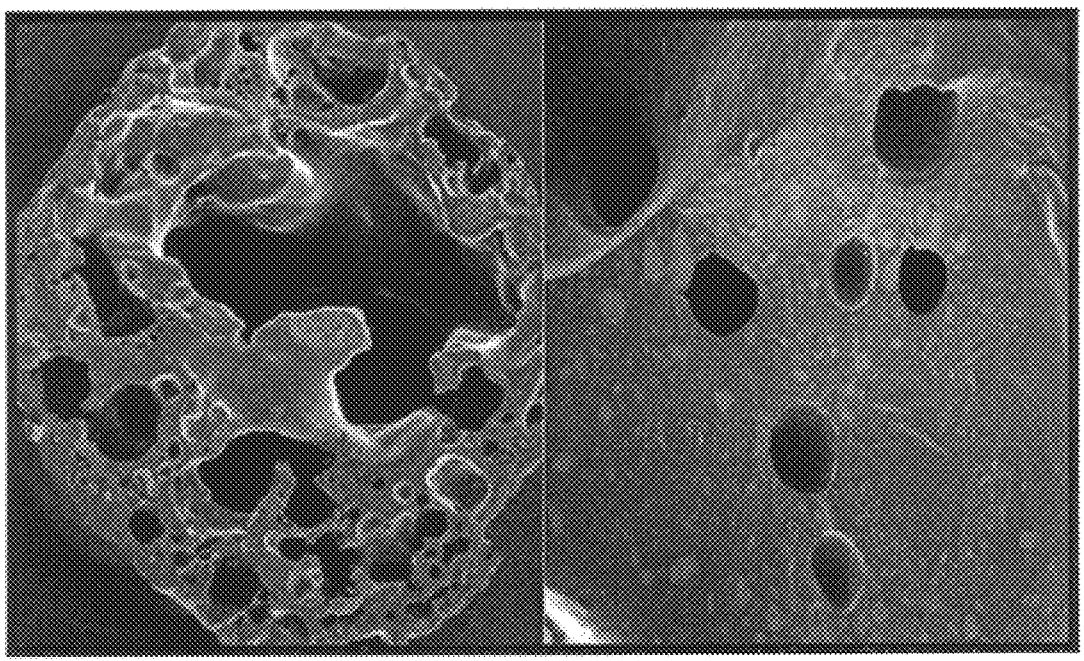
*FIG. 4A*   *FIG. 4B*
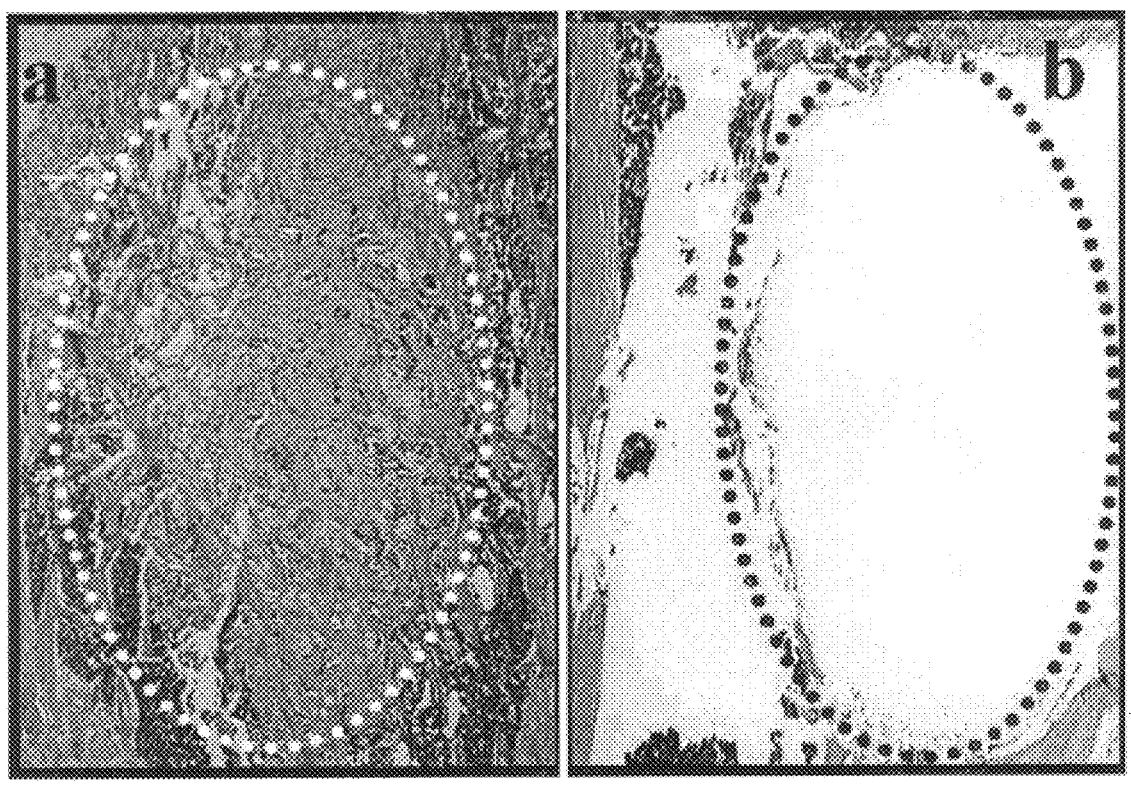
*FIG. 5A*   *FIG. 5B*

BIOERODIBLE POLYMERIC SEMI-INTERPENETRATING NETWORK ALLOYS FOR INTERNAL FIXATION DEVICES AND BONE CEMENTS

CROSS REFERENCE TO RELATED APPLICATIONS

This Application is a continuation-in-part of application Ser. No. 09/168,129 filed Oct. 7, 1998, now U.S. Pat. No. 6,153,664, which is a divisional application of application Ser. No. 08/844,378, filed Apr. 18, 1997, now U.S. Pat. No. 6,071,982; the whole of which are hereby incorporated by reference herein.

STATEMENT REGARDING FEDERALLY SPONSORED RESEARCH OR DEVELOPMENT

Not applicable

BACKGROUND OF THE INVENTION

A study in the mid-1980's estimated that about four and a half million people suffer fractures each year in the United States alone. In adults, fractures of the radius and/or ulna of the forearm, and fibula or ankle bone are frequently treated by immobilizing the fracture by the surgical attachment of a metal plate adjacent the fracture. Similarly, in some adults and most children, fractures of the neck of the femur or hip are frequently treated by immobilizing the fracture with a metal plate. In addition to its use in treating fractures of the radius, ulna and femur, metal plate may also used to immobilize other bones in both the treatment of fractures and in corrective surgery. The metal plate, typically made of a titanium-based metal, a stainless-steel, or a cobalt-chromium metal, is attached to the bone by bone screws. It should be noted that although the immobilization device is referred to as a plate, its size and shape is dictated by the application in which it is to be used.

As the bone heals it is necessary to remove the metal plate by means of a second surgical intervention. The reason for this is that the presence of the metal plate adjacent the bone ultimately results in what is referred to as "plate induced osteopenia" or loss of bone mass. The reasons for this loss of bone mass are not fully understood but appear to be related both to changes in bone stress and changes in bone blood flow. Such bone remodeling in children may lead to growth restriction, especially when plates are used in craniofacial or maxillofacial intervention to repair congenital deformities.

Thus, it is desirable to replace metallic surgical devices, e.g., plates, presently used in surgical procedures with a bioerodible polymer, i.e., one that will dissolve and be absorbed by the body as the underlying bone heals. With such a bioerodible device, the necessity of a second surgical operation and its concomitant trauma as well as the deleterious effects caused by the presence of a plate for a long period of time is removed. Furthermore, unlike metals, these devices do not corrode and the modulus of the material may be more closely matched to that of bone. Two polymers that have been used to form bioerodible surgical plates are polylactic acid (PLA) and copolymers of lactic and glycolic acids (PLGA).

The mechanism for bioeroding polymers of lactic acid and copolymers of lactic and glycolic acids is not completely understood. The polymers are probably hydrolyzed in situ to their respective monomers and the resulting monomers are excreted from the body in the urine or expired from the body as carbon dioxide without ill effect. The body's tolerance of these monomers probably results from the fact that lactic acid and glycolic acid are present as natural substances within tissue.

Although polymers of, e.g., PLA degrade as desired, plates constructed of PLA have a tendency to warp or distort in bone applications and thereby fail to appropriately immobilize fractures with respect to bending movements. This bowing apparently occurs because the side of the plate immediately adjacent the bone is exposed to a different aqueous environment than the side of the plate adjacent soft tissue. As water is adsorbed into the polymer, the polymer swells. Thus the difference in the aqueous environment of the two surfaces of the plate causes a differential in the amount of water entering the plate through each surface. This differential water adsorption results in turn in the differential swelling of the two sides of the plate, with bowing therefore occurring. Thus, it is desirable to form a surgical plate from a bioerodible polymer which is dimensionally stable.

A related matter of interest in bone repair involves ensuring that the fractured bone ends are properly stabilized when set, and maintaining this stabilization during healing. A bioerodible bone cement could be used to bridge the area of excised bone fragments and thus aid in healing. Secondly, a bioerodible bone cement could additionally be used in conjunction with bone repair proteins (BRPs) to promote active bone growth, i.e., the bone cement could function as an osteoinductive material. Also, because the rate of infection following fracture repair surgery may be as high as 11%, it would also be desirable to incorporate various antibiotics into the bone cement for slow release at the surgical site to minimize infection. Ideally, therefore, such a bone cement or "grout" should be moldable in the surgical setting, should set to form a strong solid, should stabilize at the implant site, and should support and aid the bone healing process. In conjunction with cement use or, in some cases, in place of a cement, a bioerodible internal fixation device (IFD) made of a similar material can beneficially be used to stabilize the fracture.

With the use of minimally invasive techniques, a bioresorbable and osteoconductive bone cement of low viscosity could be used by injecting the cement into the fracture site. This technique would help prevent complications such as repeated displacement, instability and malunion. The use of the cement may also warrant conservative treatment in patients with relative indications for operative management. These patients include older patients for whom mobility would be difficult in long leg casting, patients with irreducible fractures or a fracture which has slipped in a cast, patients with obese legs which limit the capability of casts to maintain reduction, and chronic alcohol abusers. In addition, patients with relative contraindications to operative treatment, such as vascular insufficiency, diabetes mellitus, soft tissue blisters, abrasions, contusions or burns, could be successfully managed in a conservative fashion, thus eliminating peri- and postoperative risk factors. Finally, patients with severe osteoporosis may benefit from the use of osteoconductive bone cement as an adjunct to conservative treatment. Aside from its use in the treatment of ankle and foot fractures, a bioresorbable and osteoconductive cement may be applicable for the treatment of undisplaced or minimally displaced lateral tibial plateau fractures that would normally warrant conservative treatment (depression<1 cm and valgus instability<10 degrees).

Other potential applications include use in spinal fusions, where autologous bone grafting is often necessary and allogeneic bone is used when autologous bone stocks are insufficient. In these cases, an osteoinductive bioresorbable bone cement could serve as a bone substitute.

Thus, a need exists for polymeric bioerodible materials which may be used in making bone cements that desirably have a wide range of precure viscosities (to allow injection of the cement to a bone site or which may be applied as a group) and that also desirably incorporate biologically active agents. Such bioerodible bone cements containing biologically active agents for release must be able to protect the agents from damage during curing and provide buffering capacity to obviate possible inflammatory foreign body response generated by bioerosion of the cement. Lastly, such polymeric bioerodible materials should also be useable to make IFDs having dimensional stability during the critical bone setting and healing period.

SUMMARY OF THE INVENTION

The invention is directed to bioerodible polymeric materials, and in particular to semi-interpenetrating network ("semi-IPN") alloys that comprise a first bioerodible polymer capable of producing acidic products upon hydrolytic degradation; a second bioerodible polymer, which, preferably via crosslinking, provides a biopolymeric scaffolding or internal reinforcement; and optionally a buffering compound that buffers the acidic products within a desired pH range. In a preferred embodiment, the second bioerodible polymer comprises polypropylene fumarate (PPF) which is crosslinked, desirably by a vinyl monomer such as vinyl pyrrolidone (VP), to form the biopolymeric scaffolding which provides the semi-IPN with the requisite dimensional stability. A beneficial end use of this material is in the form of internal fixation devices (IFDs) such as bone supports, plates, and pins. Another beneficial end use is as cured bone cements for bone repair.

A bone cement system, for making such a cured bone cement, is also contemplated within the invention. For example, a multi-part bioerodible bone cement system of the invention capable of forming a bioerodible polymeric semi-IPN alloy, comprises a first bioerodible polymer (such as PLGA) capable of producing acidic products upon hydrolytic degradation; and a second bioerodible polymer (such as PPF), which provides a biopolymeric scaffolding or internal reinforcement, wherein the second bioerodible polymer is crosslinked in vivo to provide a hardened, semi-IPN alloy bone cement.

In another aspect, a bone cement system of the invention comprises a bioerodible scaffolding polymer (such as PPF), which when polymerized provides a hardened bone cement, the cement system further comprising a gas generating agent in stabilized form for providing the cured bone cement with pores for facilitating inward cell migration.

Both the bone cements and dimensionally stable IFDs of the invention may advantageously also contain other agents such as bone repair proteins (BRPs), bone morphogenic proteins (BMPs), bone scrapings from host bone, demineralized bone, bone chips and antibiotics, to, e.g., actively promote bone growth and prevent infection while the bone cement or IFD is in place. The biologically active agents are preferably within a protective polymer envelope. Furthermore, although the usual practice involving cements requires that they be allowed to cure in situ at the surgical site, a cement material may also be cured ex situ. Ex situ curing may be conducted in molds designed for particular applications or in stock shapes such as bars or rods, which may later be machined to any desired shape.

BRIEF DESCRIPTION OF THE SEVERAL VIEWS OF THE DRAWING

The invention will be more fully understood by reference to the following Detailed Description of the Invention in conjunction with the following Drawings, of which:

FIGS. 4a and 4b are scanning electron micrographs of a PPF foaming cement according to the invention; FIG. 4a, at 15×, shows large pores measuring approximately 0.5–3 mm in diameter and FIG. 1b, at 200×, shows small pores ranging from 50–400 $\mu$m in diameter;

FIGS. 5a and 5b are photomicrographs of a longitudinal section of rat tibias in which a drill hole defect was placed; FIG. 5a shows vigorous new bone formation one week postoperative at he site of implant of the foaming bone cement according to the invention (white dotted line) while FIG. 5b shows a sham operated rat tibia in which the drill hole defect is empty (black dotted line) at three weeks postoperative;

DETAILED DESCRIPTION OF THE INVENTION

Figure 1A:
FIGS. 1a and 1b are scanning electron micrographs (at 6250×) of a bone cement alloy according to the invention containing crosslinked PPF scaffolding and PLGA/calcium gluconate after one and two weeks exposure to water.

The bioerodible bone cements and internal fixation devices (IFDs) made from the bioerodible polymeric material, disclosed herein, in particular the semi-IPN material, may advantageously be used for surgical repair of orthopaedic and maxillofacial fractures. When the bioerodible material is a polymeric semi-IPN alloy, it comprises at least a first bioerodible polymer capable of producing acidic products upon hydrolytic degradation; and a second bioerodible polymer, which upon crosslinking provides a biopolymeric scaffolding or internal reinforcement.

A semi-interpenetrating polymer network (semi-IPN) is defined herein as an intimate combination of two or more polymers, at least one of which is crosslinked (sometimes in the immediate presence of the other) to form a network ("scaffolding" in the present disclosure) in which the other polymer is enclosed, trapped or retained.

As used herein, the term "bioerodible" is defined as the susceptibility of a biomaterial to degradation over time, usually months. "Buffer" is defined as any material that controls the pH in the implant or cement and its near environment within narrow limits upon exposure to acid or base. "Acidic product" is defined herein as any product, the aqueous solutions of which have a pH less than 7.

The semi-IPN alloy of the invention includes a first bioerodible polymer that undergoes hydrolysis to produce acidic products when exposed to an aqueous medium. Examples of such bioerodible polymers include poly (lactide-co-glycolide) (H[—OCHR—CO—]$_n$OH, where R is H or CH$_3$) ("PLGA"); polydioxanone, poly($\epsilon$-caprolactone); polyanhydrides; poly(ortho esters); copoly (ether-esters); polyamides; polylactones; polypropylene fumarates (H[—O—CH (CH$_3$)—CH$_2$—O—CO—CH=CH—CO—]$_n$OH); and combinations thereof. In a preferred embodiment, the polymer poly(lactide-co-glycolide) H[—OCHR—CO]$_n$OH, R=H, CH$_3$ (PLGA) is used. The PLGA polymers used according to the invention have a lactide to glycolide ratio in the range of 0:100% to 100:0%, inclusive, i.e., the PLGA polymer can consist of 100% lactide, 100% glycolide, or any combination of lactide and glycolide residues. These polymers have the property of degrading hydrolytically to form lactic and glycolic acids.

Selection of a suitable first bioerodible polymer is based primarily on the known properties of the polymer such as polymer strength, rate of hydrolytic degradation, etc. One of ordinary skill in the art may take these and/or other properties into account in selecting a particular polymer for a particular application. Thus, such a selection of a particular polymer is within the skills of the ordinary skilled practitioner.

The second bioerodible polymer of the disclosed semi-IPN alloy may be of a type that undergoes hydrolysis to produce acidic products when exposed to an aqueous medium, such as polydioxanone, poly($\epsilon$-caprolactone); polyanhydrides; poly(ortho esters); copoly(ether-esters); polyamides; polylactones; polypropylene fumarates; other polymers capable of being crosslinked and combinations thereof. However, the second bioerodible polymer, preferably upon crosslinking, additionally provides the biopolymeric scaffolding or internal reinforcement which gives the bioerodible polymeric semi-IPN alloy its superior mechanical properties. (As such, the second polymer is desirably different from the first.) This scaffolding is desirably obtained by crosslinking the second bioerodible polymer. Crosslinking may take place, e.g., in a bone cement, shortly before or after the cement ingredients have been introduced to the bone fissure or junction. When making an alloy material for IFDs, crosslinking may be effected: a) with the first and second bioerodible polymers in cosolution via chemical crosslinking or by irradiation (e.g., $\gamma$-irradiation); b) by melt mixing the first and second bioerodible polymers, then irradiating to crosslink the second bioerodible polymer; or c) by forming the biopolymeric scaffolding first via chemical crosslinking or by irradiation, then impregnating the scaffolding with the first bioerodible polymer.

In an advantageous embodiment, the second bioerodible polymer comprises polypropylene fumarate (PPF), which may be desirably crosslinked using vinyl monomers such as vinyl pyrrolidone (VP). An advantage of VP crosslinking of PPF is that the crosslinks terminate at hydrolytically labile fumarate ester bonds, making the crosslinked network hydrolytically degradable. Furthermore, the hydrolysis products are highly soluble and hence the scaffolding (and thus the entire alloy) is truly resorbable. The crosslinking reaction should preferably seek to minimize homopolymer formation. Other crosslinking monomers such as methyl methacrylate (MMA), hydroxyethylmethacrylate (HEMA) or ethylene glycol dimethacrylate (EGDMA) may also be used as long as bioerodibility is not compromised. A high PPF:VP ratio favors crosslinking; when the crosslinking reaction is carried out in solution, lower concentrations of VP may be used to achieve a high PPF:VP ratio. The degree of crosslinking necessary to form the scaffolding will depend on the particular application, i.e., the relative hardness or rigidity desired, but generally crosslinking of about 5% to 50% of the available crosslinking sites is acceptable, more particularly 5% to 30%.

The bioerodible material of the invention may include a buffering compound which may be a base or base-generating material capable of reacting with the acidic products generated upon hydrolysis of the bioerodible polymer. Since the bioerodible polymers undergo hydrolysis in the body, they tend to generate acidic products that cause irritation, inflammation, and swelling (sterile abscess formation) in the treated area. The inclusion of buffering compounds in the bioerodible material of the invention counteracts this effect by neutralizing the acidic degradation products and thereby reducing the sterile abscess reaction. The buffering agent also minimizes the autocatalytic effect on degradation rate due to changes in pH caused by generation of acid products. The buffer included in the bioerodible material of the invention maintains the pH surrounding the area of surgery to approximately neutrality (i.e., pH 7), or any other pH as dependent on the formulation. Preferably, the pH is maintained in the range of 6–8, and more preferably in the range of 6.8–7.4.

Exemplary buffering materials include inorganic acid salts, organic acid salts, or polymeric organic acid salts. Preferably, the calcium salts of weak acids are used, such as calcium carbonate, although calcium phosphate, calcium acetate and calcium succinate may also be used. Polymeric buffers may also be used as buffering compounds according to the invention. Suitable polymeric buffers preferably include basic groups which neutralize the acidic products generated upon hydrolysis of the bioerodible polymer. Such polymeric buffers include hydrolytically stable polymers, such as polyamines, poly(N-vinyl carbazole), poly(N-vinyl pyrrolidone), salts of poly(acrylic acid), poly(acrylamide), or a copolymer based on poly(acrylic acid) salts. Another class of buffering compounds useful in the materials and methods of the invention are compounds which, on exposure to water, hydrolyze to form a base as one reaction product. The generated base is free to neutralize the acidic products produced upon hydrolysis of the bioerodible polymer. Compounds of this type include aryl or alkyl carbamic acids and imines. The base-generating compounds used according to the invention offer the advantage that the rate of hydrolysis of the base generator may be selected to correlate to the rate of hydrolysis of the bioerodible polymer.

The inclusion of certain soluble materials, (such as a combination of citric acid and sodium bicarbonate; calcium acetate, and calcium gluconate) also have an important second function in vivo. Upon exposure to aqueous media such as tissue fluids, these compounds dissolve almost immediately, leaving pores in the material, whether it be a cement or IFD. These pores facilitate bone cell migration into the device or cement, and thus serve as osteoconductive pathways for bone healing. Pore size may be controlled by controlling the size of the soluble material introduced to the alloy, i.e., by grinding and sieving the filler to select the appropriate particle size range.

Another method of forming pores is to include in the cement system a combination of materials that can interact under the right conditions, such as the exposure to a liquid, to generate a gas for foaming the mixture. In other words, these combinations of materials are "blowing agents" or gas generating agents. An exemplary combination is the citric acid and sodium bicarbonate combination, which, upon exposure to water in vivo, forms $CO_2$ and water, leaving holes in place of the solid chemical. Another example is an organic isocyanate which reacts with water to form an amine and $CO_2$. The amine can then react with more of the isocyanate to form a urea derivative according to the following reaction scheme:

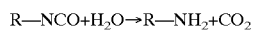

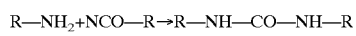

This combination may be most appropriately cured ex vivo as a molded part in order to reduce the risk of isocyanate contamination. Preferably, one of the blowing agent components is in excess to ensure complete reaction. Finally, porosity can be induced by mechanical means including stirring the uncured mixture to whip air or some other gas, e.g., nitrogen, into it. For initially low viscosity cements, the gas could be bubbled into the batch by such a means, for example, as gas dispersion tubes.

Figure 1B:

The development of such pores is illustrated in FIGS. 1A and 1B, which are SEM (Amray AMR-1000 SEM at 6250x) of a bone cement alloy containing crosslinked PPF scaffolding and PLGA/calcium gluconate after one and two weeks exposure to water. The alloy was subjected to conditions similar to placement in vivo, over a period of weeks. The development of pores in the alloy, where none were detectable at the start of the experiment, is seen. The holes measure about 3–6 microns on average, but larger holes of 10–15 microns were also seen.

It has been surprisingly found that a combination of a calcium carbonate and hydroxyapatite supports osteoconductivity and osteoinductivity, i.e., providing a pathway for bone cells to penetrate into the alloy, as well as inducing movement of bone cells into those pathways, as a way of promoting bony ingrowth as resorption of the alloy progresses.

Other fillers may be included in the alloy (preferably protected by a bioerodible polymer such as the first bioerodible polymer, as disclosed herein) as alternatives to fillers like calcium carbonate and hydroxyapatite, such as ground, demineralized bone and/or unprocessed cadaver allogenic bone.

The buffering compound preferably has an acid dissociation constant ($K_a$) that is smaller than the acid dissociation constant of the acidic products generated upon hydrolysis of the bioerodible polymer. Alternatively, the buffering compound preferably has a hydrolysis constant that is greater than the hydrolysis constant of the acidic products. Further, the buffering compound preferably is only partially soluble in an aqueous medium. In general, buffers of lower solubility are preferred because buffer loss from the polymer by diffusion will be minimized. Details of determining appropriate buffers, methods and amounts of addition, etc., are disclosed in further detail U.S. Pat. No. 5,817,328, the disclosure of which is incorporated herein by reference.

The semi-IPN alloy of the invention has mechanical properties comparable to those of trabecular (cancellous) bone as set forth in Table 1A (see entries for Cambridge Scientific bone cement).. Other mechanical properties are given in Table 1B.

TABLE 1A

COMPRESSIVE AND TENSILE STRENGTH OF VARIOUS MATERIALS

| Material | Mode | Strength, MPa |
| --- | --- | --- |
| Trabecular (cancellous) bone | Compression | 5–10 |
| Cortical bone | Compression | 150–300 |
| Cortical bone, human Cambridge Scientific | Tension | 124–174 |
| Porous bone cement | Compression | 6.8 ± 2.5; 17.7 ± 2.8* |
| Porous bone cement + 50% bone chips | Compression | 9.6 ± 2.0 |

*Compressive Modulus = 365.3 ± 74.9 MPa

TABLE 1B

MECHANICAL PROPERTIES OF VARIOUS MATERIALS

| Stiffness, | | N/mm | 1–30 |
| --- | --- | --- | --- |
| Bending: | Modulus | GPa | 6–30[1] |
| | Strength | MPa | 160 |
| Torsion: | Modulus | GPa | 3.2 (femur) |
| | Strength | MPa | 54.1 (femur) |
| Tension: | Modulus | CPa | 14.9–18.9 |
| | Strength | MPa | 124–174 |
| Compression: | Modulus | GPa | 8–9[2] |
| | Strength | MPa | 170 (femur) |

[1]Poly(L-lactide) and Poly(D,L-lactide) reinforced with calcium phosphate fibers
[2]Equine long bones Methods of making a bioerodible material for implantation into a surgical site are further contemplated by the inventors. In one embodiment, the first and second bioerodible polymers (and optional components such as biologically active agents for release into surrounding bone tissue and buffering compounds) are dissolved in solvent and mixed to homogeneity. The resulting mixture is cast into a desired form, e.g., a sheet, film, plate, screw, etc. The second bioerodible polymer is then treated to create the biopolymeric scaffolding, e.g., by crosslinking, and the solvent is evaporated while cure (crosslinking) progresses or after cure to produce a (buffered) bioerodible implantable material. The product may be further processed, for example, compacted under pressure, extruded through a die, injection molded, or shaped further into a form useful for a specific bone repair application. This is best accomplished prior to complete cure while the mixture is still somewhat plastic (capable of flow). Techniques such as compression molding may be used to form end-use configurations such as screws, plates, etc.; or stock from which IFDs may be machined. A constant pressure hydraulic press such as the Compac Model MPC-40 may be used for molding.

In another embodiment, the alloy may be prepared by methods similar to those disclosed in U.S. Pat. No. 5,456,917 to Wise et al., the text of which is incorporated by reference herein. The bioresorbable crosslinkable second polymer (e.g., poly(propylene fumarate), PPF) is dissolved in a suitable solvent (e.g., glacial acetic acid) with the crosslinking agent and initiator. The temperature is raised to induce crosslinking at a reasonable rate. When the reaction is complete, the solvent is removed by lyophilization to leave a crosslinked, porous, open celled network, resistant by virtue of its crosslinked structure to dissolution in most solvents. This solvent resistant crosslinked structure may be impregnated with a solution of the first bioerodible polymer (e.g., PLA, PLGA) by cycles of evacuation (degassing) and repressurization. Convenient solvents for this polymer include, but are not limited to, glacial acetic acid or benzene. After impregnation, the solvent is removed by a second lyophilization and the resulting semi-IPN may be further processed. Because the crosslinked network is open celled, both the network and the impregnated first polymer will comprise continuous phases.

The invention also relates to bioerodible bone cements for both orthopaedic repair and for controlled release of a biologically active agent in, if necessary, a protecting polymeric envelope. The bone cement and method of making it encompasses a range of cement materials, the properties of which depend upon the concentration of components to enable preparation of cements of initial (precure) low viscosities which can be delivered by injection to their intended sites or cements of higher viscosity which may be molded, e.g., as a putty, to fit fractures or surgical sites of complex topography.

The first bioerodible polymer, as noted above, may be loaded with an active agent to provide a controlled release of the active agent as the alloy is resorbed. Control of the release rate is achieved by incorporating the active agent in a protecting envelope of the first bioerodible polymer. In addition, further control of the release rate is achieved by incorporating non-reactive fillers of varying solubility (such as hydroxyapatite) into the alloy. Any type of active agent may be incorporated into the first bioerodible polymer, including without limitation drugs, hormones, antibiotics, cells, etc.

The bone cement of the invention comprises the first and second bioerodible polymers as set forth herein. Other desirable components of the cement include biologically active or therapeutic agent(s), a cross linking agent (such as a vinyl monomer, e.g., vinyl pyrrolidone, methyl methacrylate (MMA) or ethylene glycol dimethacrylate (EGDMA)); an initiator for the cross linking reaction between the second bioerodible polymer and the crosslinking agent; and accelerator(s) and inhibitor(s) well known to those skilled in the art, to control the cure kinetics. Further components of the material of the invention include biologically inert solid fillers, liquid (aqueous or non-aqueous) diluents for viscosity control and for solubilization of components, and wetting agents (surface active agents or detergents) to facilitate mixing of components and contact of the mixed components with tissue.

The cement may advantageously be prepared as a two or three part formulation in which the initiator and accelerator, or initiator and components for forming the scaffolding, e.g., second bioerodible polymer and crosslinker, are kept separate until the parts are combined. The combined parts are allowed to cure in situ (at the surgical or fracture site) or in the mold to aid in maintaining fracture reduction or to fill defects or other openings in bone following surgery. Keeping the system parts separate prior to use ensures against premature reaction and thus increases pre-use stability and shelf life. Guidelines for separation and packaging of components of a cement system include the following; (a) to separate initiator from an accelerator; (b) to separate initiator from liquid monomers and other liquid components; (c) to separate biologically active agents from liquid components; (d) to enable sterilization of solids by gamma irradiation and of liquids (mostly monomeric crosslinking agents) by membrane filtration; (e) to separate and/or stabilize components of any foaming agent so that foaming action does not take place until desired.

It is recognized that an accelerator, which may be a liquid, if present, is present in such limited quantities as to allow it to be absorbed into the dry components as long as such mixing does not conflict with guideline (a).

In a particularly preferred embodiment the second bioerodible polymer is PPF, which is crosslinked via polymerization between PPF and a vinyl monomer such as vinyl pyrrolidone or methyl methacrylate. The vinyl polymerization employs an initiator such as benzoyl peroxide; other initiators known to those of skill in the art may be used, such as, aziobisisobutyronitrile. Accelerators such as N,N-dimethyl-p-toluidine (DMPT) and inhibitors such as hydroquinone (HQ) or t-butylhydroquinone (TBHQ) may also be included to control cure reaction kinetics. Other components such as detergents and water may be included as processing aids to adjust viscosity and to improve workability of the cement.

The composition of the cement may be varied according to requirements of cure time, viscosity, loading of biologically active or therapeutic agent(s), and degradation rates. Component ranges (range 2=particularly preferred range) are given in Table 2.

TABLE 2

PREFERRED COMPONENT RANGES
FOR A CEMENT COMPOSITION

| Component | Range 1 (% wt) | Range 2 (wt %) |
|---|---|---|
| First bioerodible polymer | 0–50 | 3–15 |
| Second bioerodible polymer | 5–60 | 30–50 |
| Cross linking agent | 5–50 | 8–12 |
| Therapeutically inert liquid diluent | 0–50 | 10–20 |
| Active agent protected by first bioerodible polymer | 1–50 | |
| Initiator | 0–5 | 0.5–1.5 |
| Inhibitor | 0–5 | |
| Accelerator | 0–5 | |
| Water | 0–1 | |
| Detergent | 0–1 | |
| Soluble buffering material | — | 3–12 |
| Less soluble buffering material/osteoinductive agent | — | 5–20 |

One embodiment of a two part system is as follows:

| Part A (liquids) | Part B (solids) |
|---|---|
| Vinyl monomer | PPF |
| Accelerator | PLGA |
| Liquid dilutents | PLGA protected/biologically active agent(s) |
| | Inert filters |
| | Initiator |
| | Inhibitor |

This two part formulation 1) separates liquid crosslinking agent from the initiator; and 2) separates the protected biologically active or therapeutic agent(s) from the liquid components, which prevents premature release of the biologically active or therapeutic agent(s) from the first bioerodible polymer.

A typical embodiment of a three part system is shown below.

| Part A (solids) | Part B (liquids) | Part C (solids) |
|---|---|---|
| PPF | Vinyl monomer | Inert solid fillers |
| PLGA | Liquid diluents | Accelerator |
| Initiator | Inhibitor | PLGA protected/ biologically active aqent(s) |

An advantage of the three part formulation is that it separates the biologically active or therapeutic agent(s) from the initiator, which is the least thermally stable component of the cement.

As a general rule, the two part system consists of a first part comprising the dry ingredients and a second part comprising the liquid ingredients. Given below are seven examples of ways in which the system parts can be specifically organized. These examples include both a protected biologically active agent(s) and a foaming agent (or gas) generator.

| #1 | #2 | #3 | #4 | #5 | #6 | #7 |
|---|---|---|---|---|---|---|
| Parts 1 | | | | | | |
| $P_1$ | $P_1$ | $P_1$ | $P_1$ | $P_2$ | $P_2$ | $P_2$ |
| $P_1$TA | $P_1$TA | $P_1$TA | $P_1$TA | $P_1$TA | $P_1$TA | $P_1$TA |
| In | In | In | In | In | In | In |
| SB/CA | SB | CA | SB/CA | SB/CA | SB | CA |
| Parts 2 | | | | | | |
| $P_2$ | $P_2$ | $P_2$ | XLA | $P_1$ | $P_1$ | $P_1$ |
| XLA | XLA | XLA | W | XLA | XLA | XLA |
| W | CA | SB | | W | CA | SB |
| | W | W | | | W | W |

XLA = crosslinking agent, e.g., vinyl monomer
$P_1$ = polymer 1, e.g., PLGA
$P_2$ = polymer 2, e.g., PPF
In = initiator
$P_1$TA = therapeutic agent protected by $P_1$
SB/CA = sodium bicarbonate/citric acid
W = Water Incorporation of a biologically active or therapeutic agent into a coating of the first bioerodible polymer provides several advantages for the controlled release feature of the invention. The first bioerodible polymer, such as PLGA, functions as a protective coating to prevent the biologically active or therapeutic agent(s) from reacting with the components of the cement. Thus, it is possible to maintain the full potency of the biologically active or therapeutic agent(s) during the cure process. In addition, possible reactions of the biologically active or therapeutic agent(s) with the free radicals generated during the curing process is minimized because the time during which the cement changes from a fluid or viscous putty to a hard mass is short (about ten minutes). The first bioerodible polymer also functions to moderate the release of the biologically active or therapeutic agent(s). Thus, the first bioerodible polymer needs to be present in excess of the quantity needed to protect the active agent, to serve the functions of both a protective coating of the active agent and a participant in the semi-IPN alloy structure.

Combinations other than those indicated above, such as combining the monomeric crosslinking agent and the initiator, may be practiced as long as additional steps are taken to stabilize the cement system, such as storage at a temperature below the freezing point of the liquid components. In this embodiment, the uncured cement system of the invention does not need to be maintained as separate parts.

The following examples are presented to illustrate the advantages of the present invention and to assist one of ordinary skill in making and using the same. These examples are not intended in any way otherwise to limit the scope of the disclosure.

EXAMPLE 1

Experiments were conducted to demonstrate PPF crosslinking with vinyl pyrrolidone (VP) in glacial acetic acid (gl HAc) solution, in the presence and in the absence of PLGA. Glacial HAc is a suitable solvent for several reasons: 1) traces remaining in the product will not be toxic; 2) its vapor pressure at its freezing point is high (FP=16.7° C.; VP at 17.5° C. 10 mm Hg). This property allows formation of alloys of the disclosure by lyophilization to remove the solvent. Samples were prepared as shown in Table 3.

TABLE 3

|  | 40-2 | 41-1 |
|---|---|---|
| PLGA, g | — | 0.350 |
| PPF, g | 0.998 | 0.954 |
| VP, g | 2.165 | 2.167 |
| BP, g[(1)] | 0.139 | 0.139 |
| gl HAc, ml | 10 | 10 |
| Rx T° C.[(2)] | 70 | 70 |
| Rx t min[(2)] | 31 | 30–40 |

[(1)]BP = benzoyl peroxide
[(2)]Rx T° C.; Rx t min = reaction temperature and time Prior to heating, these samples were completely dissolved in gl HAc. After heating at the temperature and for the time indicated, a continuous solid phase had formed in all samples. Solubility tests on these samples indicated that crosslinking preferentially occurred over PVP homopolymer formation. Lyophilization of PPF/VP/BP and PLGA/PPF/VP/BP crosslinked in gl HAc results in porous solids.

The following describes an exemplary procedure for preparing a bioerodible semi-IPN alloy in accordance with the invention.

(a) Removal of NaOH Inhibitor from VP. VP (1-vinyl-2-pyrrolidone, Aldrich lot 07401BQ) contained 1% inhibitor of NaOH. Separation of NaOH from the VP was accomplished by a vacuum distillation of the VP/NaOH solution. The distilled VP was collected by condensing VP vapor with cold water, while the NaOH was left in the distillation flask.

(b) Crosslinking of PPF (XL-PPF) with VP in Glacial Acetic Acid. At room temperature, 1.0 g PPF [CSI, lot 48-86-2, Mw. 7277] and 1.1 g distilled VP were co-dissolved in 10 ml gl HAc (Fisher lot 905039) in a lyophilization flask. 0.13 g of a preground BP powder (Aldrich lot 06428CW) was then added to the solution in the flask. After the BP dissolved completely, the solution showed a clear amber color. The lyophilization flask was placed in a preheated silicon oil bath with a temperature of 773° C. After 15 minutes in the bath, the solution started turning white and cloudy, indicating crosslinking. After another 5 minutes in the bath, the solution became a pale yellow gel. The flask was then removed from the bath to a freezer with a temperature of −10° C. The flask was stored in the freezer for over 12 hours before it was lyophilized.

(c) Lyophilization of XL-PPF/gl HAc Solution. The lyophilization flask, now containing the frozen XL-PPF/l.c. HAc solution, was placed in an ice bath and was connected to a lyophilizer (Labconco Freeze Dryer 8) which consisted of a solvent trap and a reduced pressure at 1 mm Hg. Lyophilization proceeded until all the gl HAc was collected in the trap.

(d) Removal of Unreacted VP and PVP. The removal of unreacted compounds was accomplished by impregnating the foam with water by successive cycles of evacuation and admission of air. The washed foam was dried in an oven with a temperature set at 50° C.

(e) Impregnation of XL-PPF Foam Scaffolding with PLGA. PLGA-85:15 (PLGA-85:15, B.I. lot 25024, Mw 11500.) was introduced by immersing the foam in a solution of PLGA in gl HAc, evacuating to remove air from the foam and repressurizing to force the PLGA solution into the foam scaffolding. A second lyophilization was used to remove the gl HAc, leaving the PLGA in the scaffolding. The ratio of PLGA deposited to the foam was 52.4 w/w%.

The product was desirably washed with water to extract any PVP that had been formed. IFDs may be formed from the material as disclosed herein.

EXAMPLE 2

High viscosity cements or putties according to the disclosure using VP crosslinker were prepared as a two part formulation of variable composition, as shown in Table 4, which presents the weights of the components and the weight fractions of the PPF, calcium phosphate and VP. This example was carried out to study the cross-linking characteristics of PPF with VP and PGLA was not included.

Components of Parts A and B are summarized below:

Part A

PPF (Wt. Avg. Mol. Wt.=6650, polydispersity=2.57)
Tribasic calcium phosphate (hydroxyapatite) (approximately $Ca_{10}(OH)_2(PO_4)_6$)
Vinyl pyrrolidone (cross linking vinyl monomer)
N,N-Dimethyl-p-toluidine (accelerator)

Part B

Vinyl pyrrolidone
Benzoyl peroxide (initiator)
Hydroquinone (inhibitor)

Figure 2:
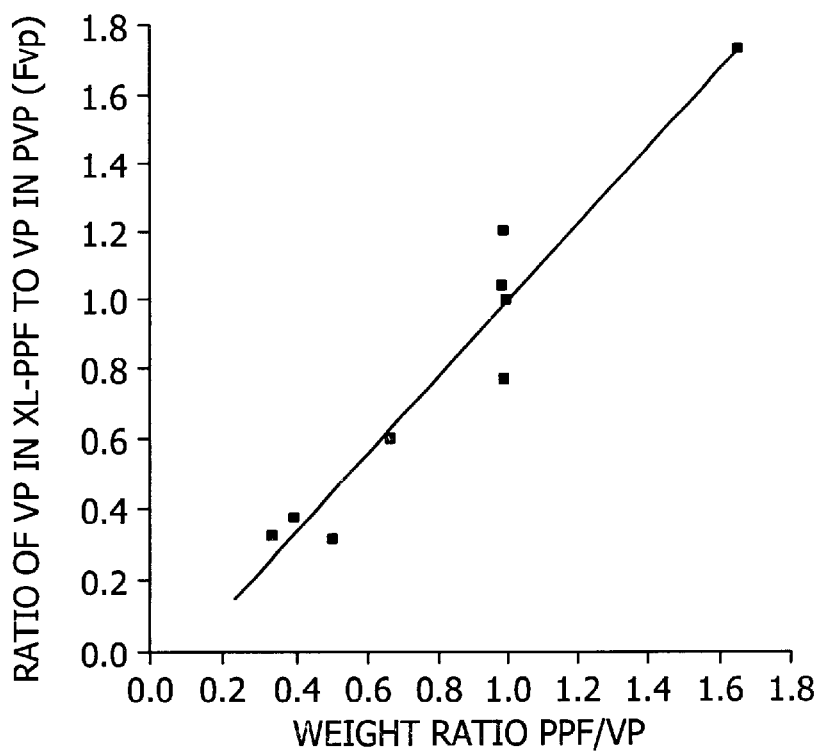
FIG. 2 is a graph showing the distribution of vinyl pyrrolidone between crosslinked poly(propylene fumarate) and poly(vinyl pyrrolidone). Linear regression analysis: intercept=−0.082; slope 1.084; correlation coefficient= 0.9686.
Figure 3:
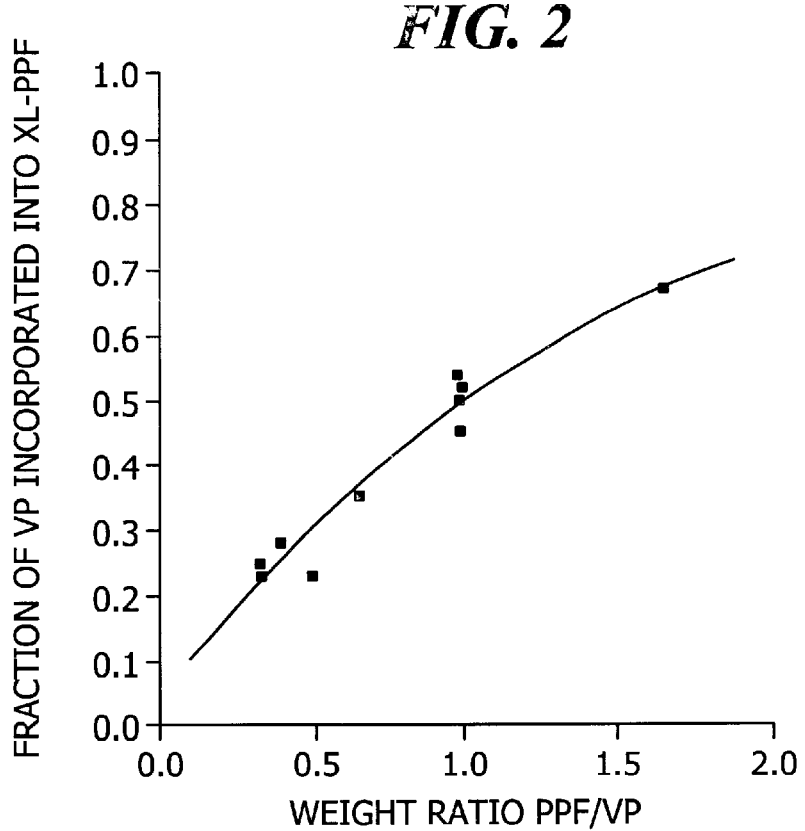
FIG. 3 is a graph showing the weight fraction of vinyl pyrrolidone incorporated into crosslinked poly(propylene fumarate) as a function of PPF/VP weight ratio.

Samples were cured in sealed vials. After curing the samples were ground, weighed, washed with water to extract soluble components, and dried to constant weight. The remaining insoluble material was then extracted with tetrahydrofuran to remove uncrosslinked PPF. In all cases almost all of the PPF was crosslinked: >98% in 6 out of 9 samples, and >86% in the remaining three samples. Further, the percent of PPF crosslinked was independent of composition, i.e., independent of filler, accelerator, initiator, or monomer. On the other hand, the fraction of VP which was incorporated into the scaffolding depended strongly on the ratio of PPF/VP, increasing with increasing PPF/VP ratio. The ratio of VP incorporated into the crosslinks varied linearly with the PPF/VP ratio. These results are summarized in Table 5 and presented graphically in FIGS. 2 and 3. The significance of these results can be appreciated if we define two quantities. The density of crosslinks between PPF chains can be defined as dcl=(moles of crosslinks/mole of PPF repeating units) and the average length of crosslinks can be defined as lcl (moles of VP/mole of PPF repeating units). Thus (dcl)=/(lcl)=(mole of crosslinks/mole of VP). Thus by varying the PPF/monomer ratio, control of the ratio (dcl)/(lcl) can be exercised.

TABLE 4

COMPOSITION OF CEMENT FORMULATIONS

| | Composition (g) | | | | | Weight Fraction | | |
|---|---|---|---|---|---|---|---|---|
| Sample | PPF* | CP | VP | BP | DMPT/VP† | f(PPF) | f(CP) | f(VP) |
| 45-75-1 | 1.0012 | 0.0000 | 1.0006 | 0.0604 | 0.0000 | 0.4855 | 0.0000 | 0.4852 |
| 45-75-2 | 1.0000 | 0.0000 | 0.6004 | 0.0604 | 0.0000 | 0.6022 | 0.0000 | 0.3616 |
| 45-75-3 | 1.0000 | 0.0000 | 1.0070 | 0.0000 | 0.0026 | 0.4831 | 0.0000 | 0.4877 |
| 45-87-2A | 1.0000 | 1.0007 | 1.0012 | 0.0605 | 0.0028 | 0.3262 | 0.3265 | 0.3275 |
| 45-87-2B | 1.0007 | 0.9997 | 1.0009 | 0.0607 | 0.0032 | 0.3265 | 0.3261 | 0.3276 |
| 45-110-1 | 1.0003 | 1.0001 | 0.5029 | 0.0605 | 0.0051 | 0.3894 | 0.3893 | 0.1978 |
| 45-110-2 | 1.0000 | 1.0004 | 2.0024 | 0.0606 | 0.0036 | 0.2459 | 0.2460 | 0.4932 |
| 45-110-3 | 1.0000 | 1.0001 | 2.9996 | 0.0603 | 0.0066 | 0.1974 | 0.1974 | 0.5933 |
| 45-132-1 | 1.0005 | 1.0000 | 1.5049 | 0.0605 | 0.0041 | 0.2803 | 0.2801 | 0.4227 |
| 45-132-2 | 1.0000 | 1.0001 | 2.4998 | 0.0600 | 0.0068 | 0.2190 | 0.2190 | 0.5489 |
| 45-123-3 | 1.0000 | 1.0007 | 3.0005 | 0.0605 | 0.0029 | 0.1974 | 0.1976 | 0.5930 |

*PPF sample 48-86-2, $M_w$ = 6651; $M_n$ = 2587, polydispersity
† Concentration of DMPT in VP = 0.48% (w/w)

TABLE 5

FRACTION OF VP AND PPF INCORPORATED INTO CROSSLINKED PPF AND DISTRIBUTION OF VP BETWEEN XL-PPF AND PVP

| Sample | PPF/VP | $Ff^\Rightarrow$ | $F\rho^\dagger$ | F_Mean ± SD‡ | $F\rho\rho f_§$ | $F\rho\rho_|$ |
|---|---|---|---|---|---|---|
| 45-75-1 | 1.0006 | 0.5554 | 0.5007 | 0.5281 ± 0.0387 | 0.9941 | 1.0038 |
| -2 | 1.6656 | 0.7097 | 0.6332 | 0.6715 ± 0.0541 | 0.9858 | 1.7260 |
| -3 | 0.9905 | 0.5725 | 0.5127 | 0.5426 ± 0.0423 |  | 1.0519 |
| -87-2A | 0.9960 | 0.4649 | 0.5463 | 0.5056 ± 0.0576 | 0.8571 | 1.2042 |
| 87-2B | 0.9966 | 0.4727 | 0.4349 | 0.4538 ± 0.0267 | 0.9773 | 0.7695 |
| -110-1 | 1.9693 |  | 0.4970 | 0.4970 |  |  |
| -2 | 0.4985 | 0.2206 | 0.2472 | 0.2314 ± 0.0153 | 0.9937 | 0.3196 |
| -3 | 0.3326 | 0.2222 | 0.2449 | 0.2336 ± 0.0161 | 0.8714 | 0.3243 |
| -132-1 | 0.56630 | 0.3272 | 0.3764 | 0.3518 ± 0.0348 | 0.8656 | 0.6035 |
| -2 | 0.3989 | 0.2893 | 0.2747 | 0.2820 ± 0.0103 | 0.9812 | 0.3787 |
| -3 | 0.3330 | 0.2238 | 0.2634 | 0.2486 ± 0.0209 | 0.9953 | 0.3297 |

$\Rightarrow$ Fraction of VP in XL-PPF calculated by material balance based on PPF.
$\dagger$ Fraction of VP in XL-PPF calculated by material balance based on VP.
‡ F = mean ± standard deviation of F| and F$\rho$ (mean F$\rho\rho f$ = 0.9469 ± 0.0619).
§ Fraction of PPF which is crosslinked.
| Distribution of VP between XL-PPF and PVP.

Varying the PPF/monomer ratio will also vary the viscosity of the cement if the crosslinking monomer is the only liquid component. However, the viscosity may be controlled independently, as described, by various diluents, which may be liquid, to reduce viscosity, or solid fillers, such as tribasic calcium phosphate (hydroxyapatite), to increase viscosity.

EXAMPLE 3

A low viscosity injectable cement may be formulated using VP both for cross linking PPF, and to control the initial viscosity. The cement can also be reformulated by substituting one of several acceptable solvents for part of the VP. In this example, this change is in Part B, which contains no monomer (VP). Acceptable solvents include propylene glycol, poly(ethylene glycol), and peanut oil. Cure rate and hardness are not compromised by this substitution. The advantages of this substitution are threefold. First, VP is miscible with these solvents as well as with water. By creating a more lipophilic environment the rate at which VP diffuses from the injection site is diminished, thus allowing a greater portion to be incorporated into the scaffolding. Minimizing diffusion into surrounding tissue is expected to diminish inflammatory response. A second advantage is that being more dilute, the probability of crosslinking with PPF is increased and that of homopolymer formation is reduced. A third advantage is increased stability. The initiator, included in Part B is now dissolved in PO rather than in the monomer VP thus eliminating premature polymerization in that part. The formulations are given in Table 6.

In this example peanut oil has been used to replace a portion of the VP, and accounts for 50% by weight of the liquid components. The Shore D hardness of IC's formulated with PO were measured as 45–50. This is comparable to polystyrene, 65; poly(ethylene), 40; and PTFE, 50.

TABLE 6

COMPOSITION OF REFORMULATED INJECTABLE BONE CEMENT (Weight %)

|  | Part A |  | Part B |
|---|---|---|---|
| PPF | 37.1 | PO | 25.1 |
| VP | 25.0 | BP | 0.6 |
| CaAc$_2$ | 12.0 |  |  |
| DMPT |  |  | 0.2 |

PPF = poly (propylene fumarate)
VP = Vinyl pyrrolidone (crosslinking agent)
CaAc$_2$ = calcium acetate (soluble filler)
DMPT = dimethyl-p-toluidine (accelerator)
BP = benzoyl peroxide (initiator)
PO = peanut oil (diluent)

The initial (precure) viscosity of the reformulated cement is determined by both the solids to liquid ratio and the viscosities of the fluid components (VP and PO). More important than the actual viscosity value is the force a surgeon must exert on the piston of a syringe containing the cement in order to expel it. To evaluate this flow rates of glycerol, peanut oil, and the injectable cement through a syringe equipped with a 15 gauge (0.137 cm i.d.) by 1.5" (3.81 cm) length were measured. Pressure on the piston was applied with weights of 0.5, 1.0, and 2.0 kg and flow of a given volume was timed. Mean flow rates under a given force are indicated in Table 7.

TABLE 7

MEAN FLOW RATES (cm$_3$/sec)

| Weight on Piston (kg) | Pressure (gram/cm$_3$) | Flow Rates, cm$_3$/sec |  |  |
|---|---|---|---|---|
|  |  | Glycerol | Cement | Peanut Oil |
| 0.5 | 283 | 0.001 | 0.001 | — |
| 1.0 | 566 | 0.054 + 0.003 | 0.169 + 0.034 | — |
| 2.0 | 1132 | 0.145 + 0.008 | 0.342 + 0.012 | 2.59 + 0.22 |

The pressure exerted by these weights, calculated by dividing the weight by the cross sectional area of the syringe barrel, are easily achieved by normal thumb pressure. The slow flow rates observed at 0.5 kg is due tothe frictional resistance of the piston. Exerting the highest pressure (1132 g/cm$^2$), 5 cc of cement can be delivered in less than 15 seconds.

EXAMPLE 4

The effect of temperature and accelerator on cure time in injectable bone cements in accordance with the invention was studied. The mixture of Example 3 was used with the following changes. VP may be used as an alternative to the crosslinking agent methyl methacrylate (MMA) and propylene glycol may be used as a solvent for PPF or as a diluent. Calcium phosphate tribasic (hydroxyapatite, "HA") is used as a relatively insoluble filler. The initiator is benzoyl peroxide and was used without an accelerator. In this example, reaction at room temperature is slow, but increases when heat is applied. In all cases the formulations are sufficiently liquid for injection. The data are shown in Table 8.

The formulations may also be varied by including an accelerator in either part A or part B, and an initiator in the other part. A soluble filler may also be included. In the examples given in Table 9 no non-reacting solvent is used. Liquid monomer (MMA or VP) but no PG is used in these formulations. The soluble filler calcium acetate (CaAc$_2$) is used in place of HA. Cure proceeds rapidly at room temperature with VP but more slowly when MMA is substituted for VP. The location of the initiator may be in either Part A or Part B as long as the accelerator is in the other part, with no effect on stability (when stored cold) or on reaction rate. Table 9 describes these formulations. All pre-cure viscosities are sufficiently low for injection.

TABLE 8

INJECTABLE CEMENTS USING PROPYLENE GLYCOL AS A NON-REACTING SOLVENT: NO ACCELERATOR

| Experiment | 1 | 2 | 3 | 4 | 5 | 6 |
|---|---|---|---|---|---|---|
| Part A | | | | | | |
| PPF:PG = 1:1*, ml | 1.0 | 1.0 | 1.0 | 1.0 | 1.0 | 0.30 |
| HA, gram | 0.2 | 0.2 | 0.4 | 0.4 | 0.6 | 0.25 |
| Part B | | | | | | |
| VP:BP = 1.0:0.5**, ml | 1.0 | 0.5 | 0.5 | 0.5 | 0.4 | 0.12 |
| Temperature, ° C. | 71 | 71 | 71 | 36 | 71 | 71 |
| Cure Time, min. | 2 | 2 | 1 | 19(hr) | 2.5 | 2.5 |

*1.0 gram PPF/1.0 ml PG
**1.0 ml VP/0.5 gram

TABLE 9

INJECTABLE CEMENTS WITH ACCELERATOR AND SOLUBLE FILLER: NO SOLVENT OR DILUENT

| Experiment | A | B | 1 | 2 |
|---|---|---|---|---|
| Part A | | | | |
| PPE*, gram | 1.50 | 1.00 | 1.50 | 1.50 |
| VP, gram | 1.00 | — | — | 1.00 |
| MMA, gram | — | 1.78 | 1.00 | — |
| CaAc2, gram | 0.10 | 1.60 | 0.10 | 0.50 |
| BP, gram | — | 0.15 | — | — |
| DMPT, gram | 0.01 | — | 0.01 | 0.01 |
| Part B | | | | |
| VP, gram | 0.50 | — | — | 0.50 |
| MMA, gram | — | 0.34 | 0.50 | — |
| BP, gram | 0.025 | — | 0.025 | 0.025 |
| DMPT, gram | — | 0.016 | — | — |
| Cure time, minutes | 0.3–0.5 | >10 | >10 | 0.5 |

EXAMPLE 5

Effect of a PPF Foaming Cement of the Invention on the Healing of Bone Defects in Vivo A composite biodegradable foaming cement based on poly(propylene fumarate) was injected into a critical size defects made in the rat tibia. Animals were divided in two groups comparing the foam in the experimental group against sham operated animals having a drill hole but no cement in the control group. Eight animals were included in each group. Animals were sacrificed at 1, 3 and 7 weeks postoperatively. Injection sites were then evaluated with histologic and histomorphometric methods. Results of this study showed that defects healed much more slowly in sham-operated animals compared to animals receiving the cement. In the experimental group, metaphyseal and cortical defects healed within the first postoperative week by formation of immature woven bone. At the site of the cortical drill hole defect, healing was noted to progress to a complete closure by formation of mature bone. Histomorphometry corroborated these findings and showed that metaphyseal bone remodeling peaked at one week postoperatively and then decreased as healing of the cortical defect progressed. Thus, near complete restoration of the original state of the tibial bone occurred in this animal model using the foaming cement of the invention.

Foaming Cement Preparation

The poly(propylene fumarate) (PPF) was synthesized by the direct esterification of fumaric acid (Fisher Scientific, Inc.) with propylene glycol (Aldrich Chemical Co., Milwaukee, Wis.). N-vinyl pyrolidone (VP) (Aldrich Chemical Co.), in an equal volume of ethanol, was added to a dry powder mixture of PPF and tribasic calcium phosphate (TCP) to form a viscous tan colored putty-like paste. Sodium bicarbonate, benzoyl peroxide initiator (Aldrich Chemical Co.), and citric acid were added in turn to produce the final foaming cement formulation whose overall composition is shown in Table 9.

TABLE 10

COMPONENT OF FOAMING CEMENT FORMULATION.

| Chemical | Wt % |
|---|---|
| Poly (propylene fumarate) | 35.4 |
| Tricalcium phosphate | 18.2 |
| Vinyl pyrrolidone | 11.7 |
| Ethanol | 11.4 |
| Sodium bicarbonate | 1.7 |
| Benzoyl peroxide | 1.6 |
| Aq. Citric Acid | 19.9 |

Approach to Cement Expandability

The reaction of citric acid (CA) and sodium bicarbonate (SB) with water produces carbon dioxide, the blowing agent responsible for foam formation and expansion. A SB/CA loading of 1% will generate an expansion of around 200% at 37° C. and 1 atm based on stoichiometric releases of $CO_2$ according to the following reaction:

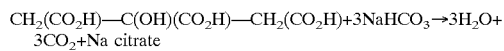
$$CH_2(CO_2H)\text{—}C(OH)(CO_2H)\text{—}CH_2(CO_2H) + 3NaHCO_3 \rightarrow 3H_2O + 3CO_2 + Na\text{ citrate}$$

Actual expansion may be less due to escape of $CO_2$ through the cement surface and/or through solution of $CO_2$ in the cement material.

Effect of VP Monomer on Crosslinking and Cement Viscosity

High ratios of PPF to VP favor incorporation of VP into a crosslinked PPF-VP network, whereas low ratios increase the probability of homopolymerization of the VP component into the water soluble poly(vinylpyrrolidone). However, as VP content is reduced, viscosity increases unless compensated for by other liquids such as water or ethanol, which are inactive. Ethanol is the better choice of solvent since water triggers immediate generation and evolution of carbon dioxide. A PPF/VP ratio of 2 will create a network with about 75% of the VP entering the crosslinks. An amount of VP equal to 35% by weight seems to provide the optimal formulation with an acceptable viscosity for injection of the foaming cement and an acceptable degree of crosslinking.

Material Properties of the Foaming Cement

Before its application in vivo, the foaming cement was characterized by scanning electron microscopy (SEM) and mechanical testing. For this purpose, pellets of the cement were allowed to cure at 37° C. in Teflon lined cylindrical molds (6 mm diameter×12 mm length) after mixing. Pellets attained constant weight after about 12 hours of vacuum drying at room temperature. The mean density computed for five samples was 0.691±0.103 (14.9 g/ml). Using 1.41 g/ml as the density of the non-porous control cement (formulated without SB/CA) yields a void volume fraction of 0.510±0.073 (±14.3%). The foaming cement was characterized by SEM. As shown in FIGS. 4a and 4b, SEM analysis of the cured PPF foaming cement pellets showed large pores measuring approximately 0.5–3 mm in diameter and small pores ranging from 50 to 400 μm in diameter.

Compressive strength and modulus were measured on an Instron Model 8511 materials testing machine equipped with a 500 lb load cell and operating at a cross head speed of 1 cm/min. The mean strength and modulus were 17.7±2.8 MPa and 365.3±74.9 MPa, respectively. These compressive strength data are comparable with values reported by Carter and Hayes, who measured this property of bone as a function of strain rate and density. At a comparable strain rate, the compressive strength of trabecular bone ($\rho=3.1$ g/cm$^3$) was noted to be 5.0 MPa, and for cortical bone ($\rho=2.0$ g/cm$^3$) was 200 MPa.

Animal Studies and Group Design

The resorbable PPF-based foam of the invention was tested using the rat tibial metaphysis implantation model according to Gerhart et al (Gerhart et al., J. Orthopo. Res. 11, 250, 1993). This model was also recently utilized by Yaszemski et al (Yaszemski et al., Tissue Engineering, 1, 41, 1995). for in vivo evaluation of PPF-cements. NIH guidelines for the care and use of laboratory animals have been observed. Adult male Sprague Dawley rats weighing approximately 400 g were used as the animal model. The formulations were evaluated by implanting foam plugs of appropriate sizes into 3-mm holes that were made into the anteromedial tibial metaphysis of rats. In this transitional portion of the rat tibia, the cortex consists of dense lamellar cortical bone and the intramedullary canal is comprised of trabecular bone forming the metaphysis. A drill hole placed at this site will therefore allow evaluation of the repair response of both dense cortical and loose metaphyseal bone to the implantation of the PPF-based foaming cement.

Animals were anesthetized using an intramuscular injection of ketamine HCl (100 mg/kg) and xylazine (5 mg/kg). The rats were also given an intramuscular prophylactic dose of penicillin G (25,000 U/kg), and the surgical site was shaved and prepared with a solution of betadine and alcohol. A percutaneous incision was made in the anterior left hind leg, and the tibial metaphysis exposed. The periosteum from the adjacent bone and the bone marrow from the ends of the tibial bone were left intact. This permitted the evaluation of the osteoconductive properties of the resorbable foam material by ingrowth through metaphyseal and periosteal bone formation. The soft tissues and skin were closed in layers with interrupted absorbable sutures.

Two groups were included in the study, allowing a comparison of the foam in the experimental group against sham operated animals having a drill hole but no implant. Eight animals were included in each group. Animals were sacrificed at 1, 3 and 7 weeks postoperatively.

Methods of Evaluation of Animal Studies

After the animals were sacrificed, 10-mm-long segments of the tibial bone including the section in which the foam material was implanted were harvested and processed for histologic analysis by fixation in 10% buffered formalin. Specimens which included residual foam material were decalcified in EDTA and were paraffin embedded. Longitudinal sections (5 μm thick) of the total specimen were then cut and stained with hematoxyline and eosin. Slides were examined for resorptive activity, new bone formation and inflammatory responses at the site where residual foam material was present.

Histomorphometry was carried out by acquiring images of serial longitudinal hematoxyline and eosin stained sections of the specimen using a CCD video camera system mounted on a Zeiss microscope. Images were digitized and analyzed using Image Pro Plus software. For each bone specimen, the total cross-sectional area of trabecular bone at both the metaphyseal and cortical drill hole sites was determined on sequential longitudinal sections. In addition, the intertrabecular space was approximated by measuring the area occupied between the bone trabeculae. A minimum of 10 sections obtained from different levels of the specimen were included for this analysis. The spacing between sections of adjacent levels was typically 300 micrometer. This allowed determination of an approximate absolute bone volume for both the metaphyseal and the cortical drill hole defect, which is given as an average percentage rate (mean ± standard deviation) of these volume measures for each bone specimen. To compare the extent of bone remodeling at the metaphyseal and the cortical drill hole defect between the experimental and the control group, the metaphyseal and cortical remodeling indices were determined. They were defined as the volume ratio of new bone and the volume of the whole defect based on eight animals per study group. They are thus given as average percentage rates.

Statistical Analysis

Differences in the remodeling index and the metaphyseal trabecular bone volume at sacrifice were analyzed for statistical significance by employing an ANOVA test. A p-level of 0.05 was considered statistically significant.

Results

Figure 6:
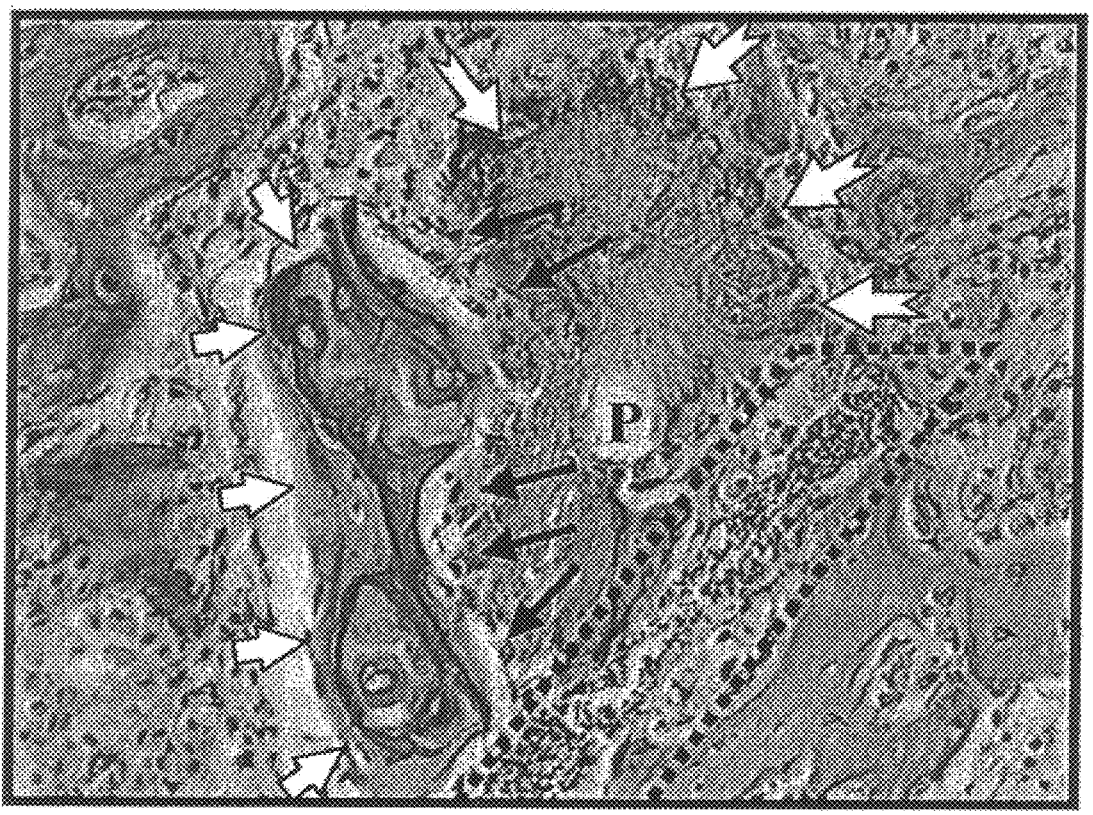
FIG. 6 is a photomicrograph of al longitudinal section of a rat tibia in which a drill hole defect was filled with a foaming cement according to the invention; the specimen was retrieved at one week postoperative and magnified 40×.
Figure 7:
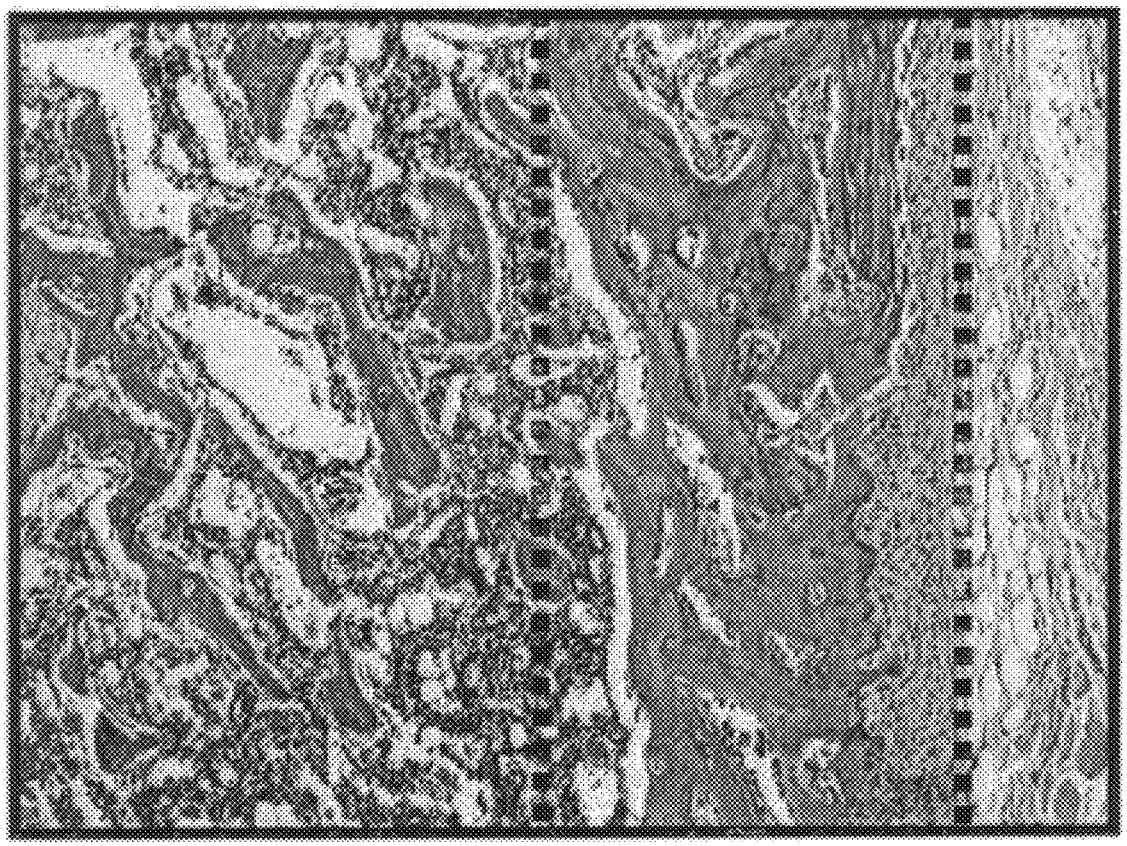
FIG. 7 is a photomicrograph of a longitudinal section of a rat tibia treated as in FIG. 6; the specimen was retrieved at one week postoperative and magnified 10×.

At one week postoperatively, there was extensive new bone formation in animals in which the foam material was implanted (FIG. 5a). The drill hole was filled with newly formed woven bone that appeared to have originated from the adjacent metaphyseal bone. The foam material was almost entirely replaced by new bone. However, residuals of the foam material were present. These foam remnants were sites of active bone formation suggesting that new bone growth was facilitated by the foam scaffold. As shown in FIG. 6, there was osteoblastic activity (black arrows) at the interface between foam remnants (outlined by white notched arrows) and newly formed woven bone trabeculae (white arrow heads). Moreover, neovascularization (capillaries outlined by black dotted line) was noted in close proximity to these foam remnants. Cells suggestive of inflammatory responses were not seen. In addition to healing of the defect made in the tibial metaphysis, there was notable bone healing at the cortical drill hole site, which is outlined with a balck dotted line. Loosely packed woven bone with wide intertrabecular spaces was present in the drill hole (FIG. 7). In comparison to the experimental group, there was no evidence of either metaphyseal or cortical bone healing in the control group (FIG. 5b) . At one week postoperatively, both the metaphyseal defect and the cortical drill hole showed virtually no new bone formation. Occasionally, there was formation of a postoperative hematoma undergoing organization with replacement by fibrous tissue and invasion of bone marrow.

Figure 8:
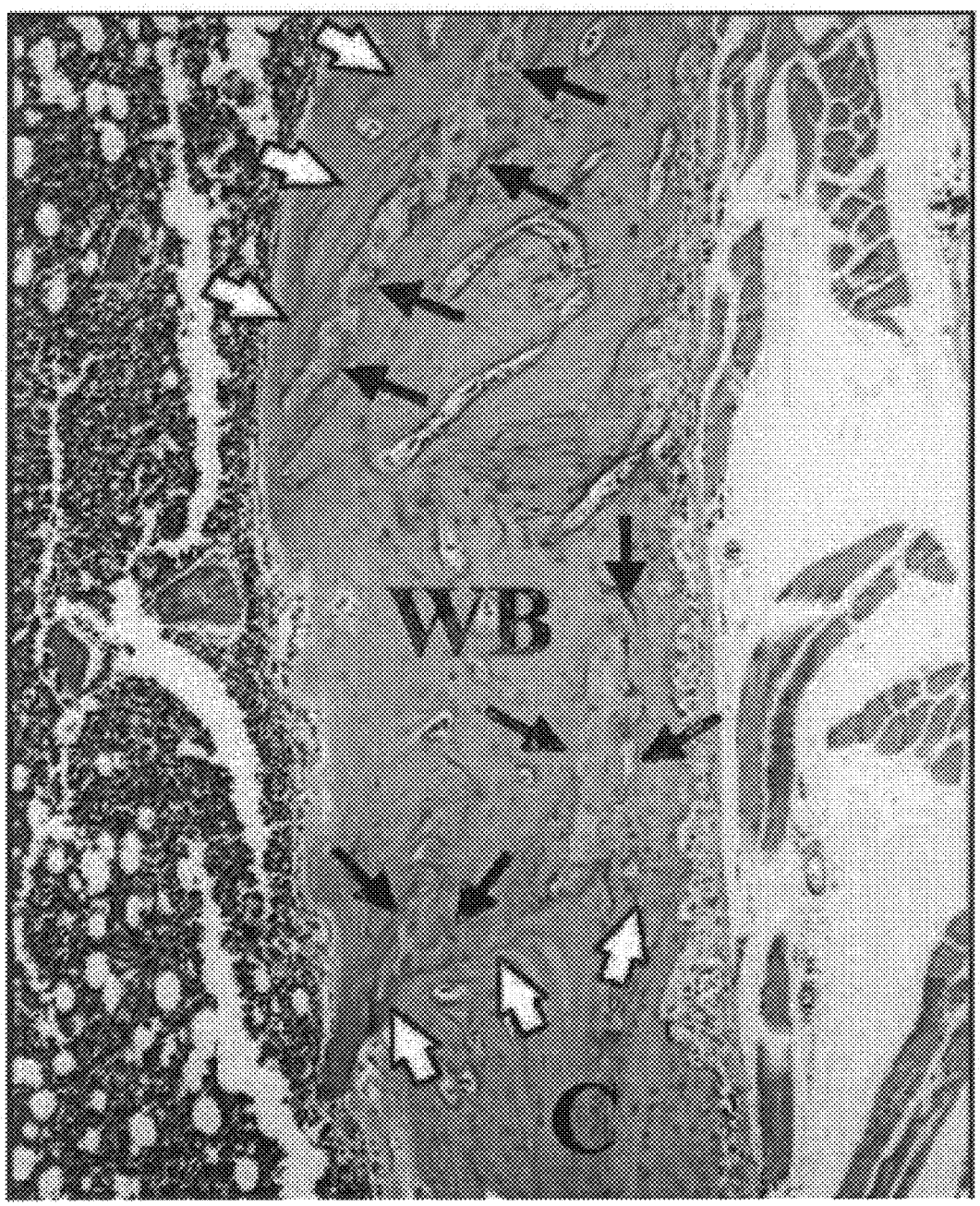
FIG. 8 is a photomicrograph of a longitudinal section of a rat tibia also treated as in FIG. 6; the specimen was retrieved at seven weeks postoperative and magnified 10×.

At seven weeks postoperatively, the entire metaphyseal area had remodeled in the experimental group resembling a normal tibial rat metaphysis (FIG. 8). Shown is the entire cortical drill hole site (outlined by white arrows) dilled with new woven bone (WB) . There is intimate contact with complete healing at both the proximal and distal rim of the drill hole through the tibial cortex (C). At these junction sites, there is endochondral bone formation as evidenced by chondrocytes (black arrows) which were noted to fill remaining intertrabecular spaces. There is no new bone present at the tibial metaphysis which is only filled with bone marrow. In the control group, there was no appreciable difference to findings noted at three weeks postoperatively.

Results of the histomorphometric analysis corroborated findings seen on histologic examination. The metaphyseal and cortical remodeling indices were determined as approximated average percentage rates based on eight animals per study group. This analysis showed that there was significantly more new bone formation in the experimental group when compared to the control group (p<0.05). Interestingly, new metaphyseal bone formation peaked at one week postoperatively and declined thereafter in the experimental group. In the control group, metaphyseal new bone formation was minimum and did not change over the postoperative follow up period. In comparison, bone formation at the cortical drill hole defect increased over time and led to complete healing of the defect in the experimental group; an observation that could not be made in the control group. The respective data for the experimental and control groups are shown in Tables 11 and 12.

TABLE 11

HISTOMORPHOMETRIC ANALYSIS OF NEW BONE FORMATION AT THE METAPHYSEAL DRILL HOLE DEFECT

| Postoperative week | Metaphyseal remodeling index [%] | |
|---|---|---|
| | Foam Injected Group | Sham Operated Group |
| 1 | 68.5 ± 14.5 | 12.3 ± 6.9 |
| 3 | 45.8 ± 11.2 | 18.4 ± 7.2 |
| 7 | 16.7 ± 7.9 | 20.1 ± 8.1 |

TABLE 12

HISTOMORPHOMETRIC ANALYSIS OF NEW BONE FORMATION AT THE CORTICAL DRILL HOLE DEFECT

| Postoperative Week | Cortical remodeling index [%] | |
|---|---|---|
| | Foam-Injected Group | Sham-Operated Group |
| 1 | 75.2 ± 10.4 | 3.1 ± 3.9 |
| 3 | 91.6 ± 6.2 | 8.5 ± 6.7 |
| 7 | 95.3 ± 4.6 | 8.6 ± 7.1 |

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. A multi-part bioerodible bone cement system comprising two or more separate parts which, upon mixing of the system parts, forms a bioerodible polymeric semi-IPN alloy, wherein a first said part comprises a first bioerodible polymer capable of producing acidic products upon hydrolytic degradation and one of said parts, which may be the same as or different from said first part, comprises a second bioerodible scaffolding polymer which upon crosslinking provides a biopolymeric scaffolding or internal reinforcement for said semi-IPN alloy; wherein one of said parts comprises crosslinking initiator and one of said parts comprises a crosslinking agent for said second bioerodible scaffolding polymer, wherein said crosslinking agent and said crosslinking initiator are in separate parts; wherein one of said parts comprises a therapeutically effective amount of a biologically active or therapeutic agent in a protective coating of a bioerodible polymer; and wherein, further, at least one of said parts comprises only dry components, at least one of said parts comprises liquid components and said biologically active or therapeutic agent is in a said part comprising only said dry components.

2. The bioerodible bone cement system of claim 1, wherein said biologically active or therapeutic agent is in a protective coating of said first bioerodible polymer.

3. The bioerodible bone cement system of claim 1, wherein said biologically active or therapeutic agent is in a protective coating of a bioerodible polymer other than said first bioerodible polymer.

4. The bioerodible bone cement system of claim 1 further comprising in one of said parts a buffering compound in sufficiently high concentration so as to buffer said acidic products within a desired pH range.

5. The bioerodible bone cement system of claim 1 further comprising in one of said parts an accelerator for said crosslinking agent.

6. The bioerodible bone cement system of claim 1 further comprising in one of said parts an inhibitor for said crosslinking agent.

7. The bioerodible bone cement system of claim 1, wherein said second bioerodible polymer comprises polypropylene fumarate (PPF).

8. The bioerodible bone cement system of claim 7, wherein said crosslinking agent is a vinyl monomer.

9. The bioerodible bone cement system of claim 8, wherein said crosslinking agent is vinyl pyrrolidone.

10. The bioerodible bone cement system of claim 7, wherein said crosslinking agent is methyl methacrylate (MMA).

11. The bioerodible bone cement system of claim 1, wherein said biologically active or therapeutic agent is selected from the group consisting of bone repair proteins, bone morphogenic proteins, bone scrapings from host bone, demineralized bone, bone chips, antibiotics, cells, and mixtures thereof.

12. The bioerodible bone cement system of claim 1, wherein said first bioerodible polymer which is not crosslinkable, is different from said second bioerodible polymer which is crosslinkable.

13. The bioerodible bone cement system of claim 1, wherein said first bioerodible polymer is selected from the group consisting of poly(lactide-co-glycolide) (PLGA); polydioxanone; poly($\epsilon$-caprolactone); polyanhydrides; poly (ortho esters); copoly(ether-esters); polyamides; polylactones; polypropylene fumarates ($H[-O-CH(CH_3)-CH_2-O-CO-CH=CH-CO-]_nOH$); and combinations thereof.

14. The bioerodible bone cement system of claim 1 further comprising in one of said parts an osteoconductive composition.

15. The bioerodible bone cement system of claim 1 further comprising in one of said parts an osteoinductive composition.

16. The bioerodible bone cement system of claim 14, wherein said osteoconductive composition comprises hydroxyapatite.

17. The bioerodible bone cement system of claim 15, wherein said osteoinductive composition comprises a component selected from the group consisting of bone repair proteins, bone morphogenic proteins, bone scrapings from host bone, demineralized bone and bone chips.

18. The bioerodible bone cement system of claim 1 further comprising a gas generating agent in stabilized form.

19. The bioerodible bone cement system of claim 18, wherein said gas generating agent is a combination of citric acid and sodium bicarbonate.

20. The bioerodible bone cement system of claim 19, wherein said citric acid and said sodium bicarbonate are in separate parts of said system, one of which is said at least one part comprising only dry components.

21. The bioerodible bone cement system of claim 19, wherein both said citric acid and said sodium bicarbonate are in said at least one part comprising only dry components.

22. The bioerodible bone cement system of claim 18, wherein said gas generating agent is an organic isocyanate.

23. A multi-part bioerodible bone cement system comprising two or more separate parts which, upon mixing of the system parts, forms a bioerodible polymeric semi-IPN alloy, wherein a first said part comprises a first bioerodible polymer capable of producing acidic products upon hydrolytic degradation and one of said parts, which may be the same as or different from said first part, comprises a second bioerodible scaffolding polymer which upon crosslinking provides a biopolymeric scaffolding or internal reinforcement for said semi-IPN alloy; wherein one of said parts comprises crosslinking initiator and one of said parts comprises a crosslinking agent for said second bioerodible scaffolding polymer, wherein said crosslinking agent and said crosslinking initiator are in separate parts; and wherein, further, at least one of said parts comprises only dry components, at least one of said parts comprises liquid components, and said system comprises a gas generating agent in stabilized form.

24. The bioerodible bone cement system of claim 23, wherein said gas generating agent is a combination of citric acid and sodium bicarbonate.

25. The bioerodible bone cement system of claim 24, wherein said citric acid and said sodium bicarbonate are in separate parts of said system, one of which is said at least one part comprising only dry components.

26. The bioerodible bone cement system of claim 24, wherein both said citric acid and said sodium bicarbonate are in said at least one part comprising only dry components.

27. The bioerodible bone cement system of claim 23, wherein said gas generating agent is an organic isocyanate.

28. A bioerodible bone cement system, the shelf-stability of which is maintained at a temperature which is below the freezing points of the components of the system and which, upon raising of the temperature of the system, forms a bioerodible polymeric semi-IPN alloy, said system comprising a first bioerodible polymer capable of producing acidic products upon hydrolytic degradation, a second bioerodible scaffolding polymer which upon crosslinking provides a biopolymeric scaffolding or internal reinforcement for said semi-IPN alloy, a crosslinking initiator and a crosslinking agent for said second bioerodible scaffolding polymer, wherein said system further comprises a therapeutically effective amount of a biologically active or therapeutic agent in a protective coating of a bioerodible polymer.

29. A bioerodible bone cement system, the shelf-stability of which is maintained at a temperature which is below the freezing points of the components of the system and which, upon raising of the temperature of the system, forms a bioerodible polymeric semi-IPN alloy, said system comprising a first bioerodible polymer capable of producing acidic products upon hydrolytic degradation, a second bioerodible scaffolding polymer which upon crosslinking provides a biopolymeric scaffolding or internal reinforcement for said semi-IPN alloy, a crosslinking initiator and a crosslinking agent for said second bioerodible scaffolding polymer, wherein said system further comprises a gas generating agent in stabilized form.

30. The bioerodible bone cement system of claim 28 or claim 29, wherein the components of said system are in separate parts.

31. The bioerodible bone cement system of claim 28 or claim 29, wherein the components of said system are in one part.

32. A multi-part bioerodible bone cement system comprising two or more separate parts which, upon mixing of the system parts, forms a bioerodible polymeric bone cement, wherein one of said parts comprises a bioerodible scaffolding polymer which upon crosslinking provides a biopolymeric scaffolding or internal reinforcement for said bone cement; wherein one of said parts comprises crosslinking initiator and one of said parts comprises a crosslinking agent for said bioerodible scaffolding polymer, wherein said crosslinking agent and said crosslinking initiator are in separate parts; wherein one of said parts comprises a therapeutically effective amount of a biologically active or therapeutic agent in a protective coating of a bioerodible polymer; and wherein, further, at least one of said parts comprises only dry components, at least one of said parts comprises liquid components and said biologically active or therapeutic agent is in a said part comprising only said dry components.

33. A multi-part bioerodible bone cement system comprising two or more separate parts which, upon mixing of the system parts, forms a bioerodible polymeric bone cement, wherein one of said parts comprises a bioerodible scaffolding polymer which upon crosslinking provides a biopolymeric scaffolding or internal reinforcement for said bone cement; wherein one of said parts comprises crosslinking initiator and one of said parts comprises a crosslinking agent for said bioerodible scaffolding polymer, wherein said crosslinking agent and said crosslinking initiator are in separate parts; and wherein, further, at least one of said parts comprises only dry components, at least one of said parts comprises liquid components, and said system comprises a gas generating agent in stabilized form.

34. A bioerodible bone cement system, the shelf-stability of which is maintained at a temperature which is below the freezing points of the components of the system and which, upon raising of the temperature of the system, forms a bioerodible polymeric bone cement, said system comprising a bioerodible scaffolding polymer which upon crosslinking provides a biopolymeric scaffolding or internal reinforcement for said polymeric bone cement, a crosslinking initiator and a crosslinking agent for said bioerodible scaffolding polymer, wherein said system further comprises a therapeutically effective amount of a biologically active or therapeutic agent in a protective coating of a bioerodible polymer.

35. A bioerodible bone cement system, the shelf-stability of which is maintained at a temperature which is below the freezing points of the components of the system and which, upon raising of the temperature of the system, forms a bioerodible polymeric bone cement, said system comprising a bioerodible scaffolding polymer which upon crosslinking provides a biopolymeric scaffolding or internal reinforcement for said polymeric bone cement, a crosslinking initiator and a crosslinking agent for said bioerodible scaffolding polymer, wherein said system further comprises a gas generating agent in stabilized form.

36. The bioerodible bone cement system of claim 34 or claim 35, wherein the components of said system are in separate parts.

37. The bioerodible bone cement system of claim 34 or claim 35, wherein the components of said system are in one part.

38. A method of making a foaming, bioerodible, polymeric bone cement, said cement comprising a crosslinked bioerodible scaffolding polymer, said crosslinked polymer providing a biopolymeric scaffolding or internal reinforcement for said polymeric bone cement, said method comprising the steps of:

providing a bioerodible scaffolding polymer;

combining said polymer with a crosslinking agent for said polymer to initiate formation of a cured cement material;

prior to cure of said cement material, introducing a gas, as a foaming agent, into said uncured cement; and permitting said cement to cure.

39. A method of making a foaming, bioerodible, polymeric semi-IPN alloy bone cement, said cement comprising a bioerodible polymer capable of producing acidic products upon hydrolytic degradation and a crosslinked bioerodible scaffolding polymer, said crosslinked polymer providing a biopolymeric scaffolding or internal reinforcement for said polymeric semi-IPN alloy bone cement, said method comprising the steps of:

providing a mixture comprising a bioerodible polymer capable of producing acidic products upon hydrolytic degradation and a bioerodible scaffolding polymer;

combining said mixture with a crosslinking agent for said bioerodible scaffolding polymer to initiate formation of a cured cement material;

prior to cure of said cement material, introducing a gas, as a foaming agent, into said uncured cement; and permitting said cement to cure.

40. The method of claim 38 or claim 39, wherein said gas is introduced into said uncured cement by vigorous stirring of said uncured cement.

41. The method of claim 38 or claim 39, wherein said gas is introduced into said uncured cement by bubbling of said gas through said uncured cement.

* * * * *